(12) United States Patent
Fan et al.

(10) Patent No.: US 10,973,465 B2
(45) Date of Patent: Apr. 13, 2021

(54) PACING SIGNAL PROCESSING METHOD, SYSTEM AND ELECTROCARDIOGRAM MONITOR

(71) Applicant: SHENZHEN MINDRAY BIO-MEDICAL ELECTRONICS CO., LTD., Shenzhen (CN)

(72) Inventors: Zhixiang Fan, Shenzhen (CN); Shen Luo, Shenzhen (CN); Pei Wang, Shenzhen (CN); Qiling Liu, Shenzhen (CN); Canwu Zhong, Shenzhen (CN); Wutao Wang, Shenzhen (CN); Yingjie Jia, Shenzhen (CN); Fang Liu, Shenzhen (CN); Xianliang He, Shenzhen (CN)

(73) Assignees: SHENZHEN MINDRAY BIO-MEDICAL ELECTRONICS CO., LTD, Shenzhen (CN); SHENZHEN MINDRAY SCIENTIFIC CO., LTD., Shenzhen (CN)

( * ) Notice: Subject to any disclaimer, the term of this patent is extended or adjusted under 35 U.S.C. 154(b) by 189 days.

(21) Appl. No.: 15/948,791

(22) Filed: Apr. 9, 2018

(65) Prior Publication Data
US 2019/0104998 A1 Apr. 11, 2019

Related U.S. Application Data

(63) Continuation of application No. PCT/CN2015/091468, filed on Oct. 8, 2015.

(51) Int. Cl.
*A61B 5/00* (2006.01)
*A61B 5/316* (2021.01)
*A61B 5/318* (2021.01)
*A61B 5/339* (2021.01)
*A61B 5/352* (2021.01)
(Continued)

(52) U.S. Cl.
CPC ............ *A61B 5/7217* (2013.01); *A61B 5/316* (2021.01); *A61B 5/318* (2021.01); *A61B 5/339* (2021.01); *A61B 5/352* (2021.01); *A61B 5/364* (2021.01); *A61B 5/366* (2021.01); *A61N 1/362* (2013.01); *A61N 1/3704* (2013.01)

(58) Field of Classification Search
USPC .................................................. 600/509–510
See application file for complete search history.

(56) References Cited

U.S. PATENT DOCUMENTS

| 5,682,902 A | 11/1997 | Herleikson |
| 7,542,794 B1 | 6/2009 | Zhang et al. |

(Continued)

FOREIGN PATENT DOCUMENTS

| CN | 2696540 Y | 5/2005 |
| CN | 102028459 | 4/2011 |

(Continued)

*Primary Examiner* — Nicole F Lavert
(74) *Attorney, Agent, or Firm* — Kory D. Christensen

(57) ABSTRACT

A pacing signal processing method, a system and an electrocardiogram (ECG) monitor, the method includes collecting at a high sampling rate the original ECG signal from a surface, obtaining the parameter and position information of a pacing signal according to the sampling points, and displaying the pacing signal morphology and/or parameter information of the pacing signal.

22 Claims, 8 Drawing Sheets

(51) Int. Cl.
*A61B 5/364* (2021.01)
*A61B 5/366* (2021.01)
*A61N 1/362* (2006.01)
*A61N 1/37* (2006.01)

(56) References Cited

U.S. PATENT DOCUMENTS

| 7,783,341 B2 | 8/2010 | Ricke et al. |
| 2010/0317985 A1* | 12/2010 | Vajdic ................ A61B 5/04012 600/523 |

FOREIGN PATENT DOCUMENTS

| CN | 102397067 A | 4/2012 |
| CN | 103860162 | 6/2014 |
| CN | 104939820 | 9/2015 |

* cited by examiner

PACING SIGNAL PROCESSING METHOD, SYSTEM AND ELECTROCARDIOGRAM MONITOR

TECHNICAL FIELD

The disclosure relates to the field of medical care, and in particular to an electrocardiogram (ECG) monitor, as well as a method and a system for cardiac pacing signal processing.

BACKGROUND ART

A cardiac pacemaker ("pacemaker") is an electronic therapeutic instrument implanted in the body for treating cardiac dysfunctions caused by certain arrhythmias. In operation, it releases electric pulses energized by a battery by means of a pulse generator to stimulate the cardiac muscles in contact with wired electrodes. For a patient having a pacemaker implanted in his or her heart, it is necessary to check the operational status of the pacemaker. Since the pacemaker can transmit wireless signals, a special test device (e.g., a programmer) may be used to wirelessly receive various operating parameters of the pacemaker and the ECG pacing pulse waveforms in the body, after which an evaluation on the operating state of the pacemaker and an adjustment on the pacemaker's operating parameter may be carried out in conjunction with the conventional surface electrocardiogram (ECG). However, since pacemakers are produced by different manufactures, they are not applicable to a same type of programmers, and thus the pacing morphology, the parameter information, as well as the operating status of the instrument and accessories are not available unless the model of pacemaker is known and then the corresponding programmer detection device is determined. Although this solution can provide evaluation, configuration, and adjustment of operating parameters of a pacemaker and can directly monitor the pacemaker, the process is troublesome and cannot be easily used for screening and monitoring.

Additionally, when ECG monitoring is performed on a patient with a pacemaker implanted in his heart, the electric signals detected on the surface also include the electric signals generated by the pacemaker other than the ECG signals generated by the heart itself. The conventional pacing pulse detection can only show whether the pacemaker has been triggered, and cannot distinguish biatrial or biventricular pacing or gain any more information, such as morphology, width, height, polarity, duration and so on of the pacemaker. Therefore, it is not possible to convincingly distinguish interference from the pacing pulses, causing medical care personnel to sometimes doubt about the accuracy of the information concerning the pacemaker's operating status.

On the other hand, the surface ECG signal from a patient with a pacemaker is mixed with the pacemaker's electrical stimulation signals. After low-pass filtering by a conventional ECG circuit, pacemaker electrical stimulation signals rich in high frequency components would lead to width broadening while attenuating the signal amplitude. The signal broadening may lead to the ECG signals in a longer period being mixed with the pacing signals so as to affect the ECG analysis. Accordingly, there is a need to remove pacing signals from the electric signals detected on the surface. With regard to biatrial or biventricular pacing, the interval between two pacing signals is very short, and the width broadening deformation of the preceding pacing signal may affect the recognition and processing of the subsequent pacing signal, i.e., the pacing detection is affected, which will consequently affect the smoothing process on the pacing signals.

SUMMARY

A pacing signal processing method is provided in one embodiment including: sampling a detected original ECG signal at a first sampling rate, to form a pacing signal morphology; acquiring position information of the pacing signal; displaying detailed information of the pacing signal according to the sampling points at the first sampling rate and the position information, the detailed information including the pacing signal morphology.

A pacing signal processing system according to one embodiment includes: a first sampling unit for sampling a detected original ECG signal at a first sampling rate to form a pacing signal morphology; a position detection unit for acquiring position information of the pacing signal; and a display unit for processing detailed information of the pacing signal into visualized information according to the sampling points at the first sampling rate and the position information, the detailed information including the pacing signal morphology.

According to one embodiment, a pacing signal processing method includes: sampling a detected original ECG signal at a first sampling rate to form a pacing signal morphology; recognizing the pacing signal according to the sampling points at the first sampling rate and characteristics of the pacing signal; acquiring position information of the pacing signal; performing a morphology analysis on the recognized pacing signal to obtain parameter information of the pacing signal; and displaying detailed information of the pacing signal according to the sampling points at the first sampling rate and the position information, the detailed information including the pacing signal morphology and/or the parameter information.

A pacing signal processing system may include: a first sampling unit for sampling a detected original ECG signal at a first sampling rate to form a pacing signal morphology; a signal recognition unit for recognizing the pacing signal according to the sampling points at the first sampling rate and characteristics of the pacing signal; a position detection unit for acquiring position information of the pacing signal; a morphology analysis unit for performing a morphology analysis on the recognized pacing signal to obtain parameter information of the pacing signal; and a display unit for processing detailed information of the pacing signal into visualized information, the detailed information including the pacing signal morphology and/or the parameter information.

According to one embodiment, an ECG monitor is provided includes: an ECG electrode for contacting a surface of a living body and detecting an ECG signal from the living body; a front-end processing device including a first sampling unit for sampling a detected original ECG signal at a first sampling rate to form a pacing signal morphology; a first back-end processing device, which may be used for recognizing a pacing signal according to the sampling points at the first sampling rate and characteristics of pacing signal, performing a morphology analysis on the recognized pacing signal to obtain parameter information of the pacing signal, and which is further used for acquiring position information of the pacing signal and processing detailed information of the pacing signal into display data according to the sampling points at the first sampling rate and the position information, the detailed information including the pacing signal morphology and/or the parameter information; and a human-machine interaction device, which is in a signal connection with the first back-end processing device and used to provide a visualized display output for a user and receive operation instruction input by the user.

In one embodiment, a pacing signal processing method includes: sampling a detected original ECG signal at a first sampling rate to form a pacing signal morphology; recognizing the pacing signal according to the sampling points at the first sampling rate and characteristics of pacing signal; performing a morphology analysis on the recognized pacing signal to obtain parameter information of the pacing signal, wherein the parameter information at least including a pulse width; acquiring position information of the pacing signal; and performing a pacing smoothing process on the ECG signal according to the position information of the pacing signal and the pulse width.

According to one embodiment, a pacing signal processing system includes: a first sampling unit for sampling a detected original ECG signal at a first sampling rate to form a pacing signal morphology; a signal recognition unit for recognizing the pacing signal according to the sampling points at the first sampling rate and characteristics of pacing signal; a morphology analysis unit for performing a morphology analysis on the recognized pacing signal to obtain parameter information of the pacing signal, wherein the parameter information at least including a pulse width; a position detection unit for acquiring position information of the pacing signal; and a smoothing processing unit for performing a pacing smoothing process on the ECG signal according to the position information of the pacing signal and the pulse width.

According to one embodiment of the disclosure, an ECG monitor includes: an ECG electrode for contacting a surface of a living body and detecting an ECG signal from the living body; a front-end processing device including a first sampling unit, which may be used for sampling a detected original ECG signal at a first sampling rate to form a pacing signal morphology; a second back-end processing device, which may be used for recognizing the pacing signal according to the sampling point at the first sampling rate and characteristics of pacing signal and performing a morphology analysis on the recognized pacing signal to obtain parameter information of the pacing signal, the parameter information at least including a pulse width, and the second back-end processing device being further used for acquiring the position information of the pacing signal and performing a pacing smoothing process on the ECG signal according to the position information of the pacing signal and the pulse width.

In one embodiment, an ECG monitor includes: an ECG electrode for contacting a surface of a living body and detecting an ECG signal from the living body; a front-end processing device, which includes a first sampling unit for sampling a detected original ECG signal at a first sampling rate to form a pacing signal morphology, and a second sampling unit for sampling a detected the original ECG signal at a second sampling rate so as to obtain an ECG signal, the second sampling rate being less than the first sampling rate; a second back-end processing device, which may be used for recognizing the pacing signal according to the sampling points at the first sampling rate and characteristics of pacing signal and performing a morphology analysis on the recognized pacing signal to obtain parameter information of the pacing signal, wherein the parameter information at least including a pulse width, and the second back-end processing module being further used for acquiring position information of the pacing signal and performing a pacing smoothing process on the ECG signal according to the position information of the pacing signal and the pulse width.

In one embodiment, a pacing signal is sampled at a surface by sampling at a high sampling rate, followed by analyzing parameter information and position information of the pacing signal, and displaying pacing signal morphology or the parameter information.

The analyzed position information of the pacing signal and the pulse width may be used for a pacing smoothing process of an ECG signal to remove a pacing signal from the ECG signal, so as to avoid the problem of incomplete or excess smoothing of pacing due to smoothing by a fixed period in the conventional pacing smoothing operation. Such a pacing smoothing method is self-adaptive, that is to say, an appropriate pacing smoothing width may be selected automatically according to the conditions of pacing signal of different patients' pacemakers so as to retain, to the greatest extent, the effective component of the ECG signal.

and

Figure 12:
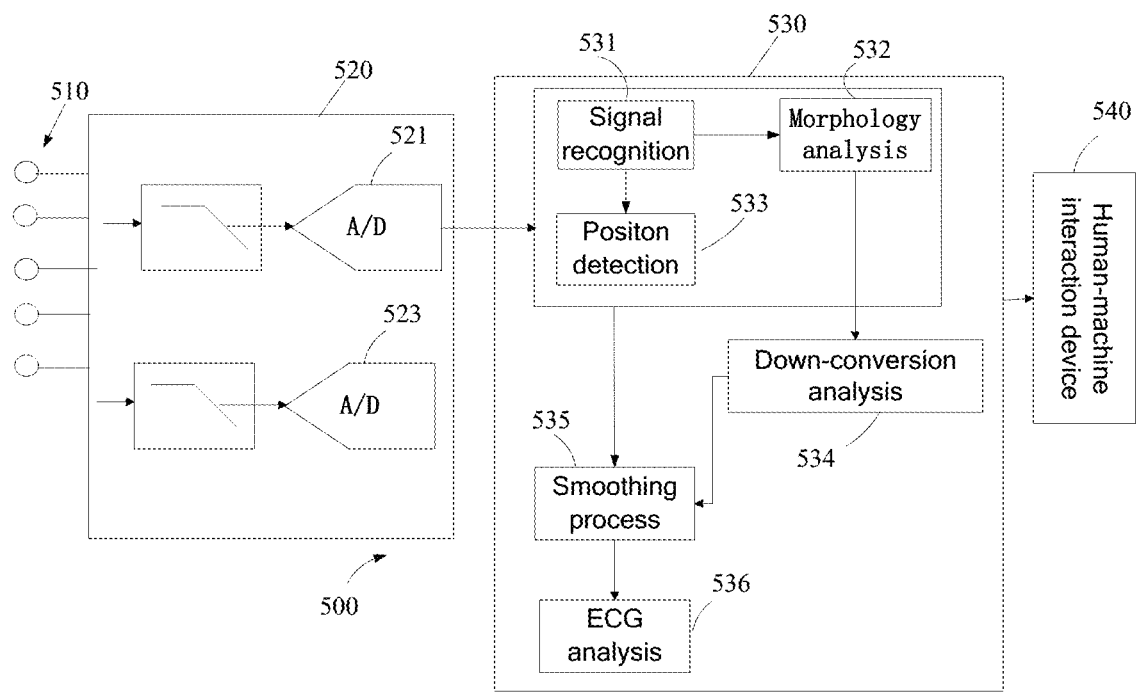

FIG. 12 is a structural schematic diagram of an ECG monitor.

DETAILED DESCRIPTION

Figure 1:
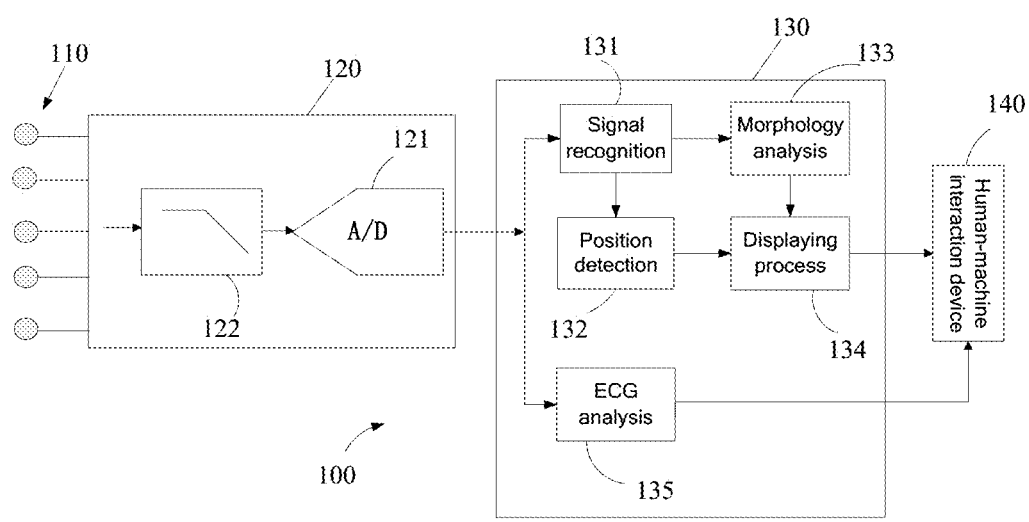
FIG. 1 is a structural schematic diagram of an ECG monitor.

Referring to FIG. 1, an ECG monitor 100 may include ECG electrodes 110, a front-end processing device 120, a first back-end processing device 130 and a human-machine interaction device 140, output ends of the ECG electrodes 110 being connected to the front-end processing device 120, an output end of the front-end processing device 120 being connected to the first back-end processing device 130, and the first back-end processing module 130 being in a signal connection with the human-machine interaction device 140.

The ECG electrodes 110 are used for contacting a surface of a living body and detecting bioelectrical signal from the surface of the living body, the bioelectrical signal being an ECG signal in this embodiment. The ECG electrodes 110 may be combined into a plurality of leads which are connected respectively to the front-end processing device 120 to output an analog ECG signal to the front-end processing device 120. In some embodiments, the ECG signal detected from the surface of the living body by the ECG leads is referred as an original ECG signal, and for a patient with a pacemaker implanted in his heart, the original ECG signal contains a pacing signal.

The front-end processing device 120 includes a first sampling unit 121, the first sampling unit 121 being used for sampling the detected original ECG signal at a first sampling rate, the pacing signal being a narrow pulse signal rich in high frequency components, and the sampling interval of the first sampling rate is far less than an pulse width of the pacing signal, so as to have enough sampling points at the first sampling rate to form a pacing signal morphology. The analog ECG signals output by the ECG leads are processed by an analog low-pass filtering unit 122 and then are input into the first sampling unit 121, and the original ECG signals detected by the leads are respectively sampled by the first sampling unit 121, the sampled data is subject to an analog-digital conversion for obtaining an digital signal, and the digital signal is input into the first back-end processing device 130.

The first back-end processing device 130 may be used for recognizing the pacing signal according to the sampling points at the first sampling rate and characteristics of pacing signal, performing a morphology analysis on the recognized pacing signal to obtain parameter information of the pacing signal, and processing detailed information of the pacing signal into visualized display data, the detailed information including the pacing signal morphology and/or the parameter information of the pacing signal. In one embodiment, the first back-end processing device 130 includes a signal recognition unit 131, a position detection unit 132, a morphology analysis unit 133, a display unit 134 and an ECG analysis unit 135. The signal recognition unit 131 may be used for recognizing the pacing signal according to the sampling points at the first sampling rate and characteristics of pacing signals; the position detection unit 132 may be used for acquiring position information of the pacing signal according to the recognized pacing signal; the morphology analysis unit 133 may be used for performing a morphology analysis on the recognized pacing signal to obtain the parameter information of the pacing signal; and the display unit 134 may be used for processing the parameter information of the pacing signal into visualized information suitable for displaying, the parameter information including at least one of pulse width, pulse height, pulse polarity, pacing duration, and distance between pacing pulse and P-QRS-T wave characteristic points. The display unit 134 can further generate pacing waveform data from the sampling points of the pacing signal for displaying. The ECG analysis unit 135 may be used for generating ECG waveform data according to the sampling data and calculating ECG parameters.

The human-machine interaction device 140 is in a signal connection with the first back-end processing device and used to provide visualized display output for a user and receive operation instruction input by the user. In one embodiment, the human-machine interaction device 140 includes a display and various input devices. The input devices are used for providing a user with input interfaces so that the user can input operation instruction by means of the input devices, e.g., a keyboard, a mouse, a touch screen, a remote control, and so on. The display may be used for providing the user with a visualized display interface, e.g., displaying an ECG waveform in a first display area, and displaying the detailed information of the pacing signal in a second display area according to a user's selection, e.g., displaying the pacing signal morphology and/or the pacing signal parameter.

The displayed pacing signal may be the pacing signal recognized in real time, e.g., each time the signal recognition unit recognizes one pacing signal, the pacing signal morphology is generated by the display unit according to the sampling points of the pacing signal, and is then displayed through the display. When the user inputs a pause instruction, the currently displayed pacing signal is on hold. When the user inputs a replay instruction, the pacing signal may be replayed from where the user specifies.

The displayed pacing signal may also be the pacing signal selected by a user, e.g., by detecting an instruction input by the user, the display unit determines an associated pacing signal according to the instruction, and shows only detailed information of the associated pacing signal.

Figure 2:
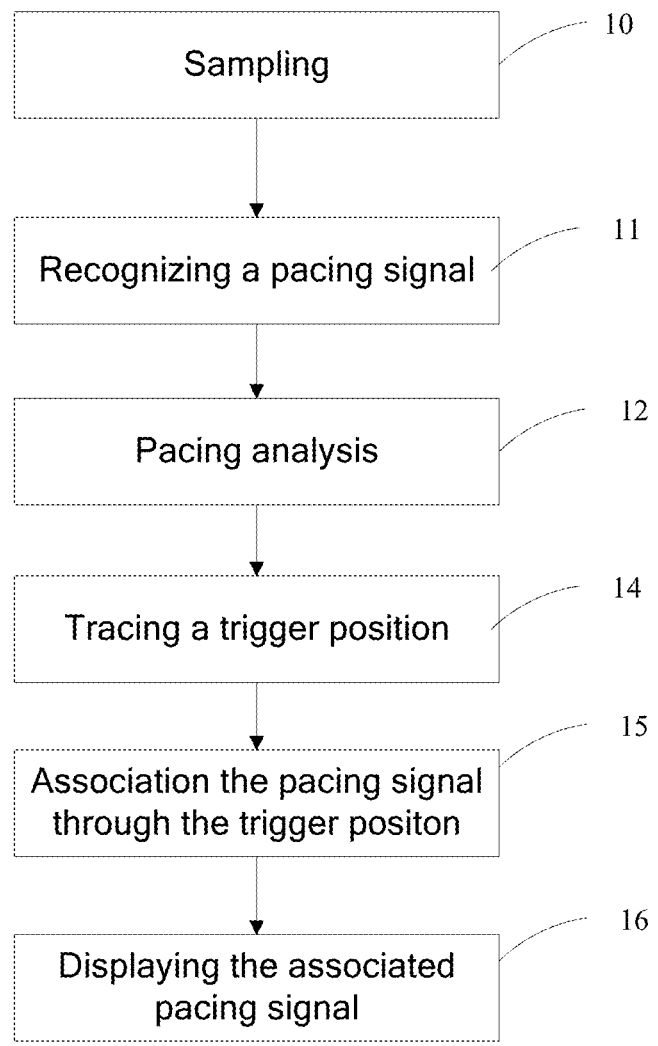
FIG. 2 is a flowchart of a method for displaying a pacing signal.

As shown in FIG. 2, a user may select the pacing signal desired to be displayed by selecting a trigger position for the pacing signal, including the following steps.

Step 10, the first sampling unit 121 samples a detected original ECG signal at a first sampling rate, wherein each sampling point being a sampled value dependent on the sampling time.

Step 11, the signal recognition unit 131 recognizes the pacing signal according to the sampling points at the first sampling rate and characteristics of pacing signal, e.g., the signal recognition unit 131 recognizes a pacing signal by means of a slope detection. Since the pacing signal is a very steep high-frequency pulse signal as compared with ECG signal of the heart itself, it is considered that the pacing signal is detected when a difference between consecutive adjacent sampling points exceeds a preset threshold.

Step 12, analyzing the pacing signal. The morphology analysis unit 133 performs the morphology analysis on the recognized pacing signal so as to obtain the parameter information of the pacing signal, the parameter information including the width, height and polarity of the pacing pulse, the pacing duration, and the distance between pacing pulse and P-QRS-T wave characteristic points. In addition, the position detection unit 132 can obtain the position information of the pacing signal according to the sampling points of the recognized pacing signal. In one embodiment, after the morphology analysis of the pacing signal, an array of the pacing signal including the parameter information and the position information of the pacing signal may be generated.

Step 14, marking a trigger position. On the one hand, high frequency sampling points are used for recognizing the pacing signal. On the other hand, the ECG analysis unit generates the ECG waveform according to the sampling points and displays the ECG waveform in the first display area through the human-machine interaction device 140. When the pacing signal is recognized, the position detection unit 132 marks a trigger position for the pacing signal on the ECG waveform according to the position information of the pacing signal, and the marking may reflect pacing characteristics, such as polarity, single-chamber pacing, biatrial pacing or biventricular pacing. The trigger position marking may be carried out in such a way of using a special mark, as shown in FIG. 3, using flags, to mark a trigger position for the pacing signal, with a flag pointing up indicating a positive polarity, with a flag pointing down indicating a negative polarity, with flags on both top and bottom indicating positive-negative bipolarity, and with two opposite flags indicating the biatrial pacing or the biventricular pacing.

Step 15, associating the pacing signal through the trigger position. The user may select the trigger position of the pacing signal, for which detailed information is desired to be displayed, by means of a mouse, a touch screen and a moving window, for example, In one embodiment, a user's click operation may be captured through focuses preset in the first display area, so as to obtain the trigger position selected by the user. In one embodiment, a solid triangle is used to mark the pacing signal selected by the user, as shown in FIG. 3. The display unit detects the trigger position selected by the user on the ECG waveform, and since the array of each pacing signal contains position information, the matched array of the pacing signal may be found through the position information so as to determine the associated pacing signal.

Figure 3:
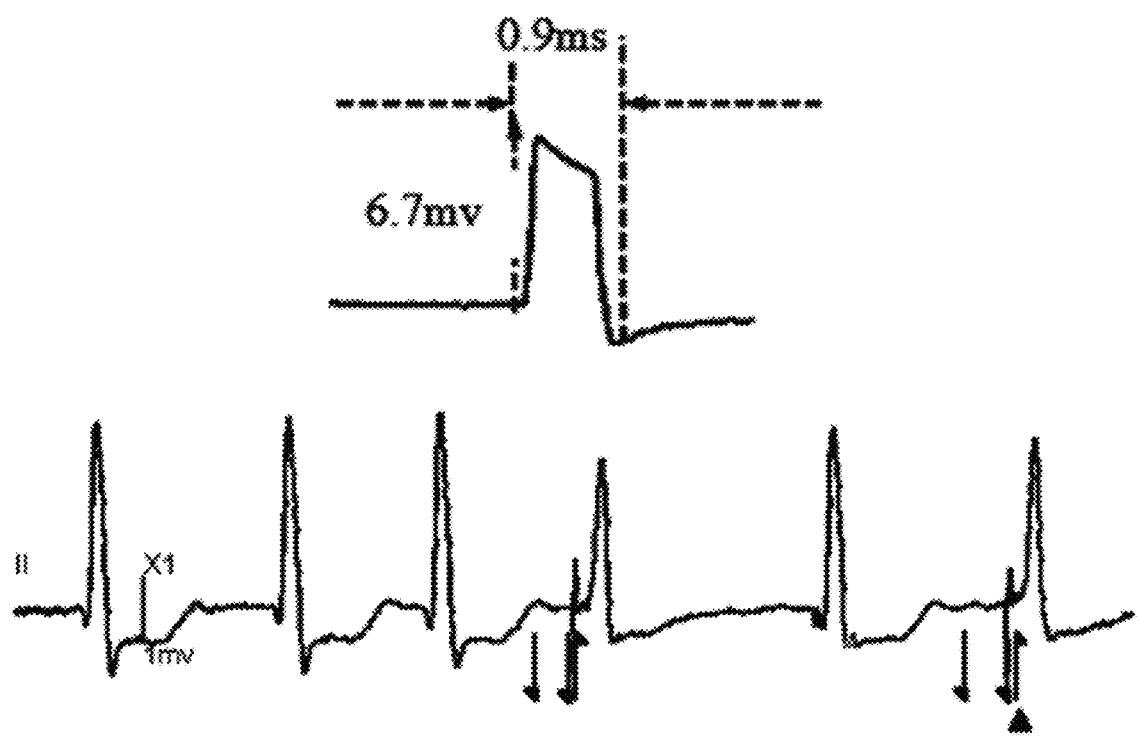
FIG. 3 is a schematic diagram of displaying a pacing signal according to a selected trigger position.

Step 16, displaying the detailed information of the associated pacing signal in the second display area, as shown in FIG. 3, and the ECG waveform is displayed in the first display area. When the user selects the trigger position of the rightmost pacing signal, the display unit 134 performs a displaying process on the recognized pacing signal according to the sampling points at the first sampling rate, the position information and the pulse width, and the human-machine interaction device 140 displays in the second display area the detailed information of the pacing signal at the trigger position according to the data output by the display unit 134, the detailed information including the pacing signal morphology and the numerically described pulse width of 0.9 ms and height of 6.7 mv.

Figure 4:
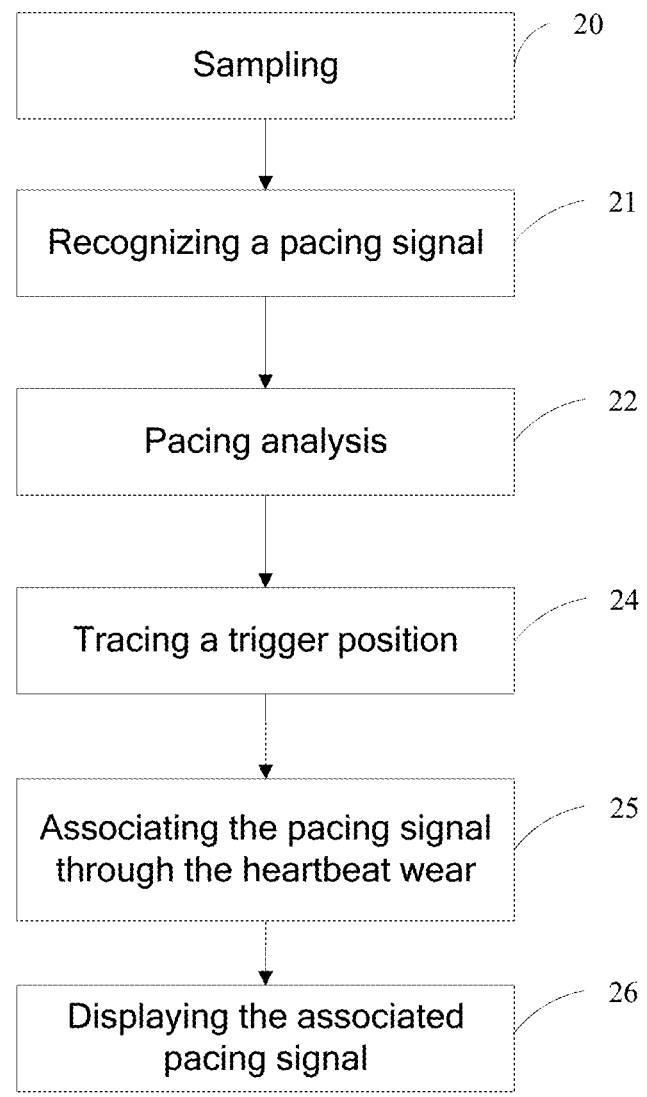
FIG. 4 is a flowchart of a method for displaying a pacing signal.

FIG. 4 is a flowchart of a user selecting a pacing signal desired to be displayed by selecting one heartbeat wave (i.e., one P-QRS-T wave) on the ECG waveform, and may include the following steps.

Step 20, the first sampling unit 121 samples the detected original ECG signal at the first sampling rate.

Step 21, the signal recognition unit 131 recognizes the pacing signal according to the sampling points at the first sampling rate and characteristics of pacing signals.

Step 22, analyzing the pacing signal. The morphology analysis unit 133 performs the morphology analysis on the recognized pacing signal so as to obtain the parameter information of the pacing signal. The parameter information includes the width, height and polarity of the pacing pulse, the pacing duration, and the distance between the pacing pulse and P-QRS-T wave characteristic points. In addition, the position detection unit 132 can obtain the position information of the pacing signal according to the sampling points of the recognized pacing signal. After the analysis, the array of the pacing signal may be generated, the array includes the parameter information and the position information of the pacing signal.

Step 24, marking the trigger position. The position detection unit 132 marks the trigger position for the pacing signal on the ECG waveform according to the position information of each pacing signal.

Step 25, associating the pacing signal through the heartbeat wave. The user can select the certain heartbeat wave on the ECG waveform by means of the mouse, the touch screen, the moving window and so on, the display unit 134 determines all the pacing signals of the heartbeat wave according to the distance between the pacing signal and the adjacent P-QRS-T wave characteristic point. For example, if the distance between the pacing signal and the previous heartbeat wave is greater than the distance between the pacing signal and the subsequent heartbeat wave, the pacing signal is considered to belong to the subsequent heartbeat wave.

Figure 5:
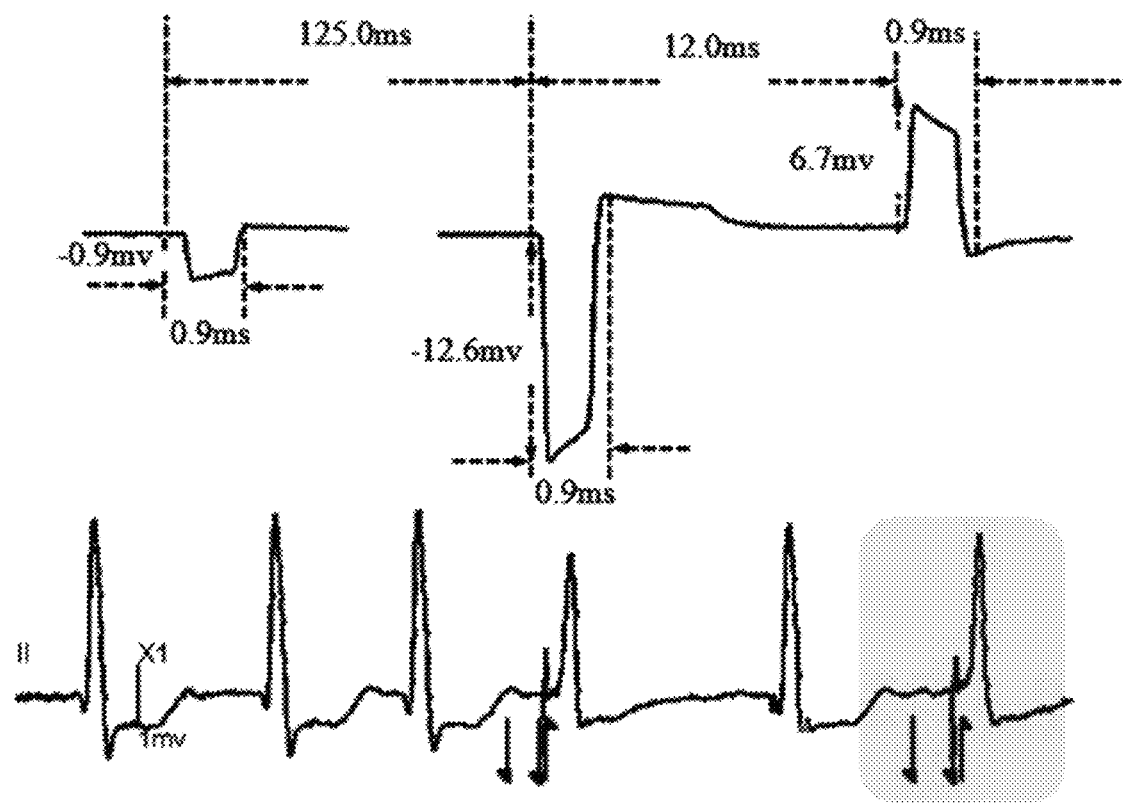
FIG. 5 is a schematic diagram of displaying a pacing signal according to a selected P-QRS-T wave.

Step 26, displaying the detailed information of the associated pacing signal in the second display area, as shown in FIG. 5, and the ECG waveform is displayed in the first display area. When the user selects one heartbeat wave through the moving window (for example, a gray box in the figure), the detailed information of all the multiple pacing signals of the heartbeat wave is displayed in the second display area, the detailed information including the pacing signal morphology, the numerically described pulse width and height, and the distance between the pacing signal and the adjacent pacing signal.

It should be appreciated by those skilled in the art that, for the case of determining the associated pacing signal by selecting a heartbeat wave, in some embodiments, step 24 may not be included. In some embodiments, the detailed information of one or more of all pacing signals in the heartbeat wave or the pacing signals of multiple heartbeat waves may also be displayed.

The parameter information of the pacing signal and the pacing waveform may be displayed together with the ECG waveform or displayed individually. Furthermore, the parameter information and the pacing signal morphology may be displayed simultaneously or displayed individually, with the parameter only or the pacing signal morphology only. The parameter may be displayed in any suitable way.

In some embodiments, the parameter information of the pacing signal further includes pacing types, which includes A-single atrial pacing, V-single ventricular pacing, VV-biventricular pacing, AV-single atrial and single ventricle pacing, AVV-single atrial and biventricular pacing, and AAVV-biatrial and biventricular pacing. According to the interval and duration between the current heartbeat wave and the pacing wave, or P, QRS and T wave information of the pacing wave and the heartbeat wave, the pacing type may be determined and displayed.

After passing through the body tissue, the signal generated from the pacemaker may have different mapping changes on different ECG leads, and even are different in amplitude, morphology and noise degree. A display of the surface pacing signals in multiple lead directions may be provided to allow medical personnel to observe. For example, with the ECG waveform and the pacing signal being displayed simultaneously in one window, the user can switch between different ECG leads and then select one heartbeat wave band on the chosen lead, and thus all the pacing signals and the parameter information on the heartbeat wave may be shown in the window.

The displayed pacing signal may be a waveform collected from the surface pacing signal, or a waveform by superposition or averaging of multiple pacing waveforms. The superposition of multiple pacing signals means the superposition of the detailed information of the same type of pacing signals collected at the same trigger position by various ECG leads. The averaging of multiple pacing signals means the averaging of the detailed information of multiple pacing signals of the same type collected by the single ECG lead during the preset period. The superposition is for viewing the pacing signals from multiple leads at same time, and the averaging means the averaging of multiple pacing signals of the same type from one lead during a period of time, with the propose of the averaging being to improve the signal-to-noise ratio of pacing signal displayed.

In this embodiment, by sampling the analog signals output from the ECG leads at the high sampling rate, the pacing signal morphology and the parameter of the pacing signal may be obtained by analysis, and the pacing signal may be accurately distinguished from interference by means of the repeatability of the pacing pulse signal morphology, the randomness of interference and the specificity of the pacing pulse signal morphology.

In addition, the surface pacing signals or some important parameter information of the pacemaker may be presented by graph or text, so as to help the clinicians to, on the basis of confirming the accuracy of the pacing signal detection (being an interference or a pacing pulse), further understand the working conditions of the pacemaker in the patient, including whether the pacemaker output is effectively captured, position of the lead wire and whether the lead wire in normal operation.

Figure 6:
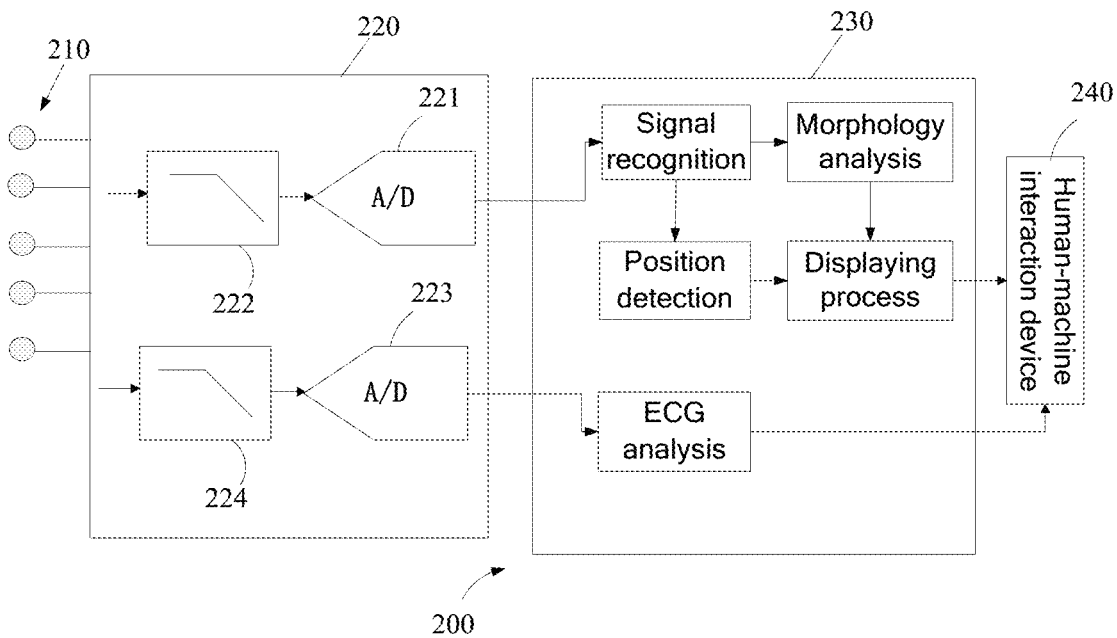
FIG. 6 is a structural schematic diagram of an ECG monitor.

Referring to FIG. 6, an ECG monitor 200 may include ECG electrodes 210, a front-end processing device 220, a first back-end processing device 230 and a human-machine interaction device 240, the output ends of the ECG electrodes 210 being connected to the front-end processing module 220, the output end of the front-end processing device 220 being connected to the first back-end processing device 230, and the first back-end processing device 230 being in a signal connection with the human-machine interaction device 240.

Different from the ECG monitor 100 of the embodiment shown in FIG. 1, in this embodiment, the front-end processing device 220 includes a first sampling unit 221 and a second sampling unit 223. In one embodiment, the ECG signals detected by the ECG electrodes 210 are processed in two ways. In one way, the ECG signal detected by the ECG electrodes 210 are processed by an analog low-pass filtering unit 222 and input into the first sampling unit 221, the first sampling unit 221 samples the detected original ECG signal at a first sampling rate so as to obtain high frequency sampling points, and the collected signals are input into the first back-end processing device 230 for the pacing signal recognition. In the other way, the ECG signal detected by the ECG electrodes 210 are processed by an analog low-pass filtering unit 224 and input into the second sampling unit 223, the second sampling unit 223 samples the detected original ECG signal at a second sampling rate, and the collected signals are input into the first back-end processing device 230 for generating the ECG waveform, the second sampling rate being less than the first sampling rate, for example, the second sampling rate is the conventional sampling rate, the first sampling rate may be several times of the second sampling rate, and the sampling points obtained at the second sampling rate are low frequency sampling points.

In this embodiment, the original ECG signal is sampled respectively at a high and a low sampling rate, the high frequency sampling points are used for detecting the pacing pulse, and the low frequency sampling points are used for generating the ECG waveform, thereby reducing the complexity and data computation of the back-end ECG analysis.

Figure 7:
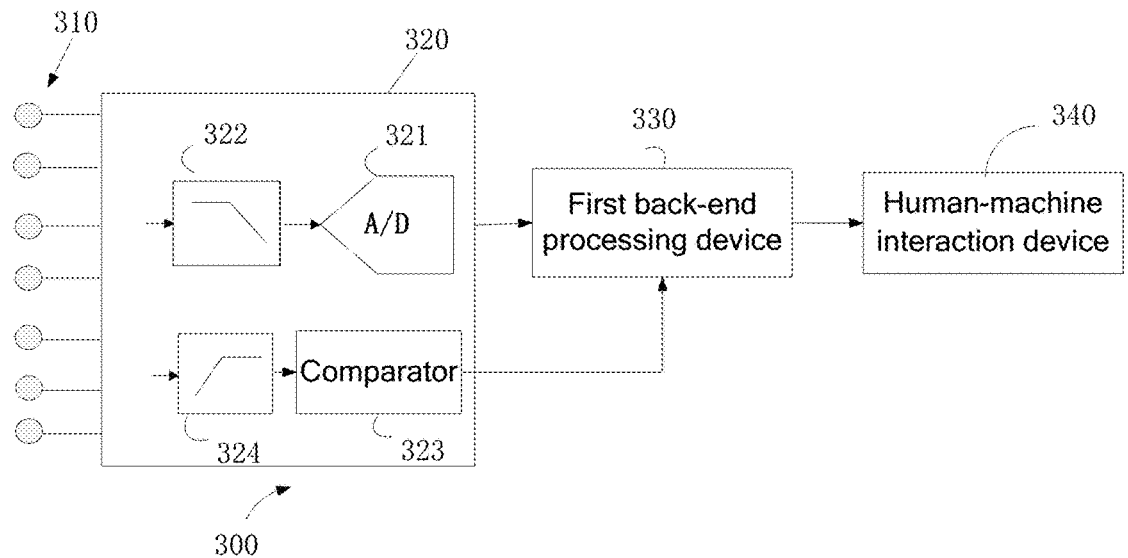
FIG. 7 is a structural schematic diagram of an ECG monitor.

In one embodiment, the trigger position for the pacing signal is obtained by hardware detection. Referring to FIG. 7, the ECG monitor 300 includes ECG electrodes 310, a front-end processing device 320, a first back-end processing device 330 and a human-machine interaction device 340, the front-end processing device 320 including a first sampling unit 321 and a pacing hardware detection unit. In this embodiment, the pacing hardware detection unit includes a high-pass filter 324 and a comparator 323 connected electrically to each other. In one embodiment, the ECG signals detected by the ECG electrodes 310 are processed in two ways. In one way, the ECG signal detected by ECG electrodes 310 are processed by an analog low-pass filtering unit 322 and input into the first sampling unit 321, the first sampling unit 321 samples the detected original ECG signals at the first sampling rate so as to obtain high frequency sampling points, and the collected signal is input to the first back-end processing device 330. In the other way, the ECG signal detected by the ECG electrodes 310 are processed by an analog high-pass filter 324 to filter out the heartbeat signals and retain the pacing signal rich in high frequency components, the signal processed by high-pass filtering is input to a first input end of the threshold comparator 323, a second input end of threshold comparator 323 is connected to a reference level for providing a comparison threshold, the first back-end processing device 330 determines the trigger position of the pacing signal according to the level output by the pacing hardware detection unit so as to obtain the position information of the pacing signal, and meanwhile, the pacing pulse morphology analysis is performed on the sampled values output by the front-end processing device 320 so as to obtain the parameter information of the pacing signal.

In this embodiment, when only the pacing signal morphology is displayed, it is not required to perform a morphology analysis on the pacing signal or calculate the parameter information of the pacing signal, and instead, the display unit acquires sampling points during a preset period before and after the position information according to the position information of the pacing signal and processes the sampling points during the preset period into waveform data, and the human-machine interaction device 340 displays the pacing signal morphology according to the waveform data output by the display unit.

Figure 8:
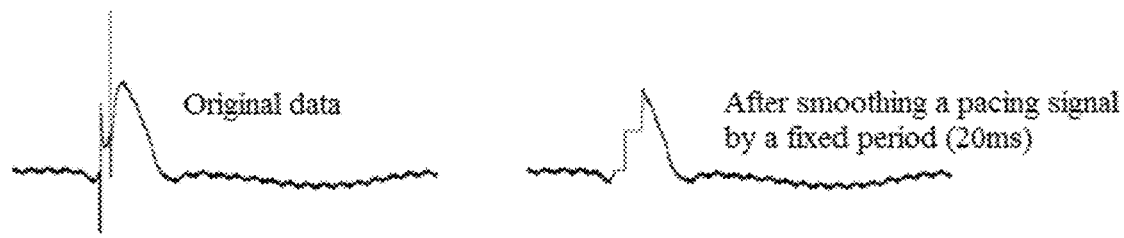
FIG. 8 shows an ECG waveform before and after smoothing with a fixed time.

In one embodiment, since the data collected from the original ECG signal contains electrical stimulation information of the pacemaker, the ECG waveform formed based on the sampling signals is also affected by the pacing pulse, as shown in FIG. 8, where the graph on the left shows the ECG waveform formed from the original data, with the pacing signal being superposed on the ECG signal. In order to display the ECG waveform generated by the heart itself, the pacing smoothing process may be performed on the ECG waveform, i.e., removing the pacing signal superposed on the ECG signal. In one solution, a fixed period (e.g., 20 ms) is preset as the pacing pulse width, and then flattening is performed on the trigger position of the pacing signal, from the start point of the pacing pulse, by the fixed period, as shown in FIG. 8, where the graph on the right shows the effect after smoothing the pacing signal in the graph on the left. Since the smoothing is performed on the ECG signal, with the trigger position of the pacing signal as a central point, by the fixed period, the pacing signal do not necessarily have the same pulse width for different patients or different pacemakers, which causes the problem of incomplete or excess pacing smoothing. For example, it may be seen from FIG. 8 that the pulse width of the pacing signal in FIG. 8 is less than the fixed period of 20 ms, and after a smoothing process by the fixed period of 20 ms, a step-like distortion appears on the ECG waveform.

In this embodiment, the pacing signal smoothing is performed with an adaptive pulse width which varies with the pulse width of the pacing signal.

Figure 9:
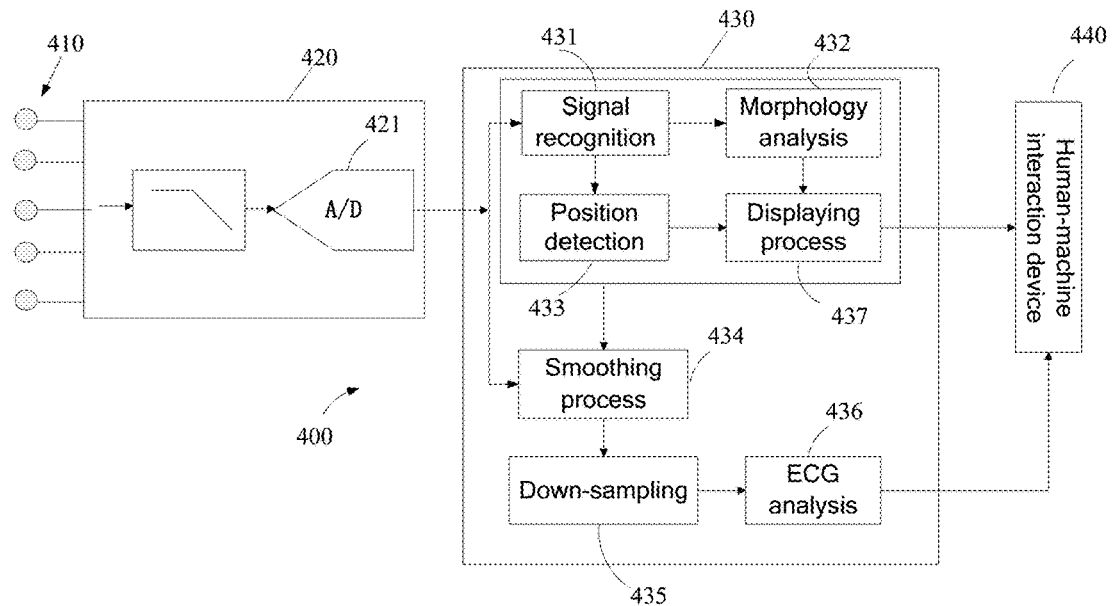
FIG. 9 is a structural schematic diagram of an ECG monitor.

Referring to FIG. 9, an ECG monitor 400 of this embodiment includes ECG electrodes 410, a front-end processing device 420, a second back-end processing device 430 and a human-machine interaction device 440, the output ends of the ECG electrodes 410 being connected to the front-end processing device 420, the output end of the front-end processing device 420 being connected to the second back-end processing device 430, and the second back-end processing device 430 being in a signal connection with the human-machine interaction device 440.

The ECG electrodes 410 are the same as those in the above-mentioned embodiments, and will not be described in detailed.

The front-end processing device 420 includes a first sampling unit 421. The first sampling unit 421 may be used for sampling the detected original ECG signal at a first high frequency sampling rate. On the one hand, the sampling points are used for the pacing analysis. In addition to the pacing signal recognition and the trigger position detection, the pacing analysis also requires information on various parameters of the pacing signal, so that it is required that the first sampling rate is high enough to collect as many sampling points as possible during the pacing pulse so as to form the pacing signal morphology. On the other hand, the sampling points are used as the basic data for generating the ECG waveform.

The second back-end processing device 430 may be used for recognizing the pacing signal according to the sampling points at the first sampling rate and characteristics of the pacing signal, and performing a morphology analysis on the recognized pacing signal to obtain parameter information of the pacing signal, the parameter information at least including the pulse width, and the second back-end processing device 430 is further used for acquiring the position information of the pacing signal and performing the pacing smoothing process on the ECG signal according to the position information of the pacing signal and the pulse width.

Figure 10:
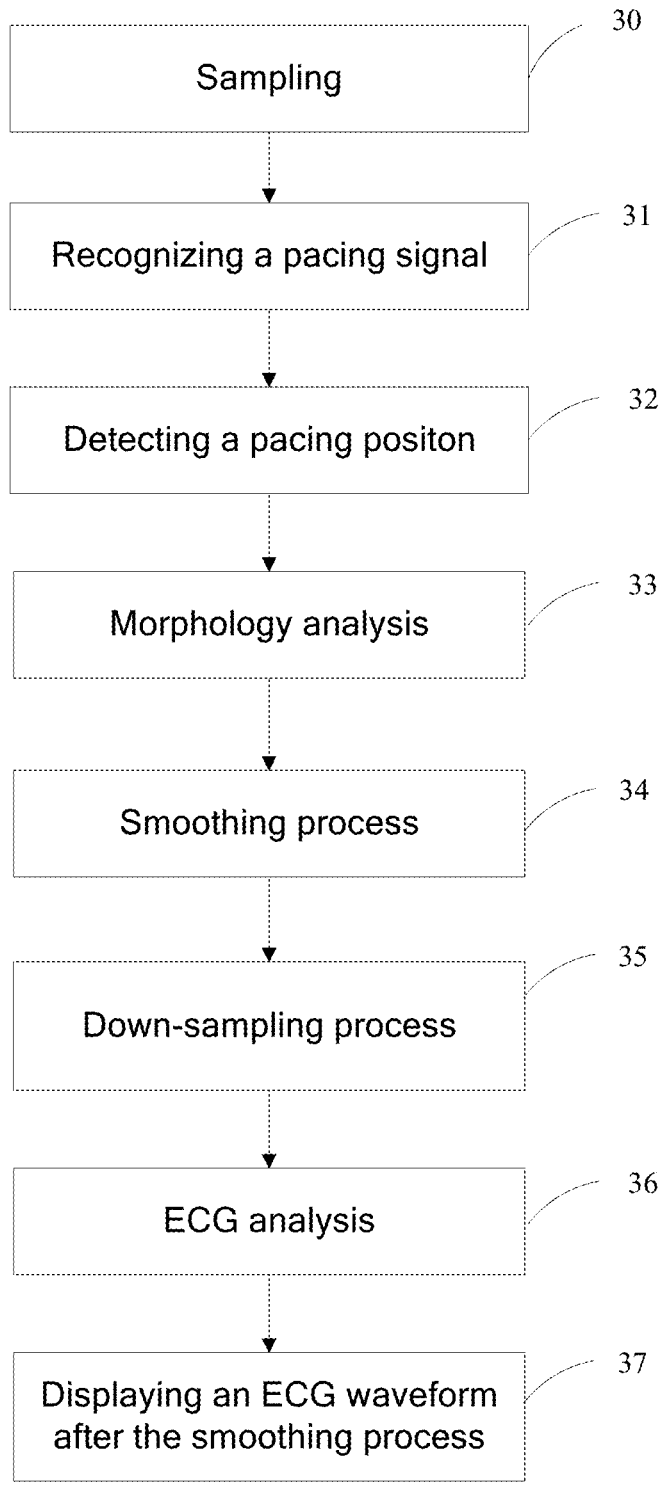
FIG. 10 is a processing flowchart of the ECG monitor.

In one embodiment, the second back-end processing device 430 includes a pacing analysis unit, a smoothing processing unit 434, a down-sampling unit 435 and an ECG analysis unit 436. The pacing analysis unit includes a signal recognition unit 431, a morphology analysis unit 432 and a position detection unit 433. The processing flow of the ECG monitor 400 is as shown in FIG. 10, including the following steps.

Step 30, the detected original ECG signal is sampled at a first sampling rate.

Step 31, recognizing a pacing signal. The signal recognition unit 431 recognizes the pacing signal according to the sampling points obtained at the first sampling rate and characteristics of the pacing signal.

Step 32, detecting a pacing position. The position detection unit 433 acquires the position information of the pacing signal after the pacing signal is recognized by the signal recognition unit 431.

Step 33, calculating the parameter information. The morphology analysis unit 432 performs the morphology analysis on the recognized pacing signal so as to obtain the parameter information of the pacing signal.

Step 34, performing the smoothing process. The smoothing processing unit 434 performs the pacing smoothing process on the ECG signals according to the position information of the pacing signal and the pulse width, specifically including determining the trigger position of the pacing signal on the ECG waveform according to the position information of the pacing signal, starting from the pacing pulse at the trigger position as the starting point, and performing the smoothing process using the pulse width of the pacing signal.

Step 35, performing a down-sampling process. The down-sampling unit 435 may be used for a down-sampling process on the ECG signal after the pacing smoothing process on the ECG signal, for example, to reduce the sampling points from the first sampling rate to the second sampling rate, so as to reduce the subsequent data processing amount of the ECG analysis unit 436.

Step 36, performing an ECG analysis. The ECG analysis unit 436 processes the data after the down-sampling process so as to form the ECG waveform data, and calculates the ECG parameter.

Step 37, displaying the ECG waveform after the smoothing process.

It should be appreciated by those skilled in the art that, among the steps mentioned above, the order of the steps 32 and 33 may be reversed.

In another embodiment, the second back-end processing device 430 further includes a display unit 437, as shown in FIG. 9. The morphology analysis unit 432 performs the morphology analysis on the sampling points of the recognized pacing signal, and calculates the parameters of the pacing signal, e.g., the pulse width, height and polarity, the interval between pacing pulses, and the distance between the pacing pulse and P-QRS-T wave characteristic points, so that the user can use a solution in the above embodiments to select the pacing signal desired to be displayed, and the display unit 437 is used to perform visualization on the sampling points and the parameter information of the pacing signal and displays for the user through the human-machine interaction device 440.

Figure 11:
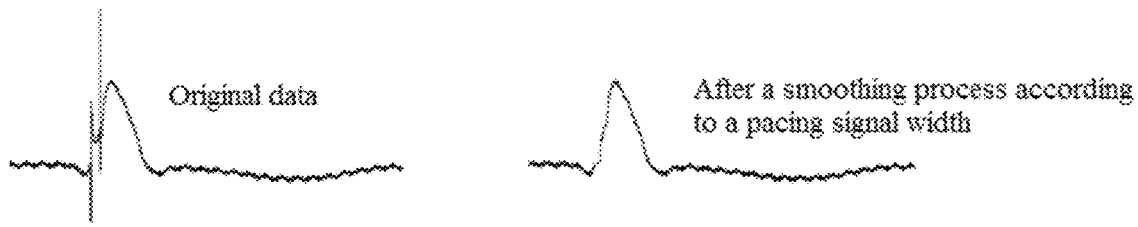
FIG. 11 shows an ECG waveform after smoothing with an adaptive time.

In this embodiment, since the position of the pacing signal and the pulse width may be obtained by the high frequency sampling, and the pacing signal may be smoothed in the subsequent smoothing process using the actual pulse width and the position of the pacing signal, the pacing signal superposed on the ECG signal may be removed accurately, thereby avoiding excess or less smoothing for the pacing signal. In addition, in this embodiment, the pacing signal and the ECG signal are both collected at the high sampling rate and subjected to the smoothing process using the high frequency sampling points, and the ECG waveform after the smoothing process is subjected to the down-sampling process before an ECG algorithm analysis, so as to avoid the problem of width broadening due to the low-pass filtering on the high frequency signal. FIG. 11 shows an effect diagram of the pacing ECG waveform smoothed by the actual width of the pacing signal. Such a pacing smoothing method is self-adaptive, that is to say, an appropriate pacing smoothing width may be selected automatically according to the different patient's pacemakers and the conditions of the actual surface signals so as to retain, to the greatest extent, the effective components of the ECG signal. This embodiment represents another solution of performing pacing signal smoothing using the adaptive pulse width. That is to say, the pacing analysis is performed in the way of high frequency sampling, while the ECG sampling is still performed in the conventional way of low frequency sampling, which can accurately recognize the pacing signal (including biatrial and biventricular pacing) by the high frequency pacing sampling without increasing the processing complexity and data amount of the ECG signal. However, as the pacing signal is down-converted from the high frequency to the lower frequency, the pulse width thereof will be broadened accordingly. Therefore, in this embodiment, an evaluation is carried out on the broadening width of the pacing signal before the smoothing process.

As shown in FIG. 12, the ECG monitor 500 of this embodiment includes ECG electrodes 510, a front-end processing device 520, a second back-end processing device 530 and a human-machine interaction device 540. The front-end processing device 520 is the same as the front-end processing device 220 of the above embodiment, and includes a first sampling unit 521 and a second sampling unit 523. The first sampling unit 521 samples the detected original ECG signal at the first sampling rate, and the collected signal is input into the second back-end processing device 530 for the pacing analysis. The second sampling unit 523 samples the detected original ECG signal at the second sampling rate, and the collected signal is input as the ECG signal into the second back-end processing device 530. Among others, the first sampling rate is less than the second sampling rate.

The second back-end processing device 530 includes a signal recognition unit 531, a morphology analysis unit 532, a position detection unit 533, a down-conversion analysis unit 534, a smoothing processing unit 535 and an ECG analysis unit 536. The signal recognition unit 531, the morphology analysis unit 532 and the position detection unit 533 are respectively the same as those of the above embodiments, and are used for the pacing analysis on the sampling points obtained at the first sampling rate. The down-conversion analysis unit 534 may be used for analyzing the width broadening due to the down-conversion of the pacing signal to the ECG sampling frequency, including calculating firstly the difference between the first sampling rate and the second sampling rate, and then calculating the pulse width of the broadened pacing signal according to the difference as well as the pulse width and height of the pacing signal detected at the first sampling rate and combined with the sampling bandwidths at the two sampling rates. The smoothing processing unit 535 performs a pacing smoothing process on the ECG signals according to the position information of the pacing signal and the broadened pulse width, and the ECG analysis unit 536 performs an ECG analysis on the ECG signals after the smoothing process and displays the ECG waveform through the human-machine interaction device 540.

For the pulse width of the broadened pacing signal, in addition to using the actual calculated width, the level selection can also be used to determine the pulse width after broadening. For example, in one embodiment, as the first and second sampling rates and the corresponding sampling bandwidths are fixed, a look-up table may be pre-designed to divide the broadening width of the pacing signal into several levels, e.g., four levels of 5 ms, 10 ms, 15 ms and 20 ms, each of the broadening levels corresponding to an interval of the pulse width and height of the pacing signal detected at the first sampling rate. Therefore, in another embodiment, the down-conversion analysis unit 534 may further determine the width interval according to the pulse width and height of the pacing signal detected at the first sampling rate, so that the broadening level of the pacing signal may be determined from the look-up table.

In this embodiment, a balance between the processor resource and the smoothing process is achieved by the down-conversion analysis for the pacing signal and the subsequent pacing smoothing process using the pulse width of the broaden pacing pulse, thereby reducing the processor resource utilization while avoiding the excess smoothing as possible.

It should be appreciated by those skilled in the art that, in the above embodiments, the position information of the pacing signal may also be obtained by hardware, for example, using the solution of the above embodiment to obtain the position information of the pacing signal.

It is to be understood by those skilled in the art that all or some of the steps of the various methods in the embodiments described above could be achieved by hardware, such as a CPU, instructed by a program, which program may be stored in a non-transitory computer-readable storage medium. The storage media may include read-only memories, random access memories, disks or optical disks, etc.

The present disclosure has been described in detail with reference to specific examples, which are merely for the purpose of facilitating understanding of the disclosure and are not intended to limit the disclosure. It will be apparent to those skilled in the art that changes may be made to the specific embodiments described above in accordance with the teachings of the disclosure.

What is claimed is:

1. A method performed by an electrocardiogram (ECG) monitor for evaluating an operational state of a pacemaker implanted in a patient, comprising:
   detecting an original ECG signal including a bioelectrical signal generated by a heart of the patient and a pacing signal generated by the pacemaker;
   sampling, by a front-end processing device, the detected original ECG signal at a first sampling rate to form a pacing signal morphology, wherein a sampling interval of the first sampling rate is smaller than a pulse width of the pacing signal;
   acquiring, by a first back-end processing device, position information of the pacing signal; and
   displaying, in a first area by an ECG analysis unit, an ECG waveform corresponding to the original ECG signal, wherein the ECG waveform is obtained from the original ECG signal using a second sampling rate that is less than the first sampling rate;
   displaying, in a second area by the first back-end processing device, detailed information of the pacing signal according to sampling points at the first sampling rate and the position information, the detailed information including the pacing signal morphology.

2. The method of claim 1, further comprising:
   recognizing the pacing signal according to the sampling points at the first sampling rate and characteristics of the pacing signal; and
   performing a morphology analysis on the recognized pacing signal to obtain parameter information of the pacing signal;
   wherein detailed information further including the parameter information of the pacing signal.

3. The method of claim 2, wherein the parameter information of the pacing signal comprises at least one of pulse width, height and polarity, pacing duration, pacing type, and a distance between pacing pulse and P-QRS-T wave characteristic point.

4. The method of claim 2, wherein the parameter information comprises the pulse width of the pacing signal, and wherein displaying detailed information of the pacing signal according to sampling points at the first sampling rate and the position information comprising: displaying detailed information of the recognized pacing signal according to sampling points at the first sampling rate, the position information and the pulse width.

5. The method of claim 2, wherein the parameter information comprises pulse width, and the method further comprising: performing a pacing smoothing process on an ECG signal according to the position information of the pacing signal and the pulse width.

6. The method of claim 5, further comprising: acquiring the ECG signal according to the sampling points at the first sampling rate.

7. The method of claim 6, wherein after performing a pacing smoothing process on an ECG signal further comprising: performing down-sampling processing of the ECG signal.

8. The method of claim 5, further comprising: acquiring the ECG signal according to the sampling points at a second sampling rate, and the second sampling rate being less than the first sampling rate.

9. The method of claim 1, wherein acquiring position information of the pacing signal comprises one of the following steps:
obtaining the position information of the pacing signal recognized by means of a digital software; and
inputting the pacing signal in the original ECG signal and a preset threshold value into a comparator for comparison, and detecting the position information according to an output lever of the comparator.

10. The method of claim 1, wherein displaying detailed information of the pacing signal according to sampling points at the first sampling rate and the position information comprising:
acquiring sampling points during a preset period before and after the position information, and
performing a pacing signal morphology displaying process on the sampling points of the preset period.

11. The method of claim 1, wherein the detailed information of the pacing signal comprises detailed information of a single pacing signal, a superposition of a plurality of pacing signals, or an average of a plurality of pacing signals, wherein the superposition of the plurality of pacing signals includes superposing the detailed information of the pacing signals of same type at same trigger position collected by different ECG leads, and wherein the average of the plurality of pacing signals includes averaging the detailed information of the pacing signals of same type collected by a single ECG lead during a preset period.

12. The method of claim 1, wherein displaying the detailed information of the pacing signal according to the sampling points at the first sampling rate and the position information comprising:
determining an associated pacing signal according to a user's selection and the position information of the pacing signal, and displaying the detailed information of the associated pacing signal according to the sampling points at the first rate and the position information.

13. The method of claim 12, wherein determining an associated pacing signal according to a user's selection and the position information of the pacing signal, and displaying the detailed information of the associated pacing signal according to the sampling points at the first rate and the position information comprising:
according to the position information of the pacing signal, marking a trigger position for the pacing signal on an ECG waveform in a first display area; and
detecting the trigger position for the pacing signal on the ECG waveform selected by the user, and displaying in a second display area the detailed information of the pacing signal corresponding to the trigger position according to the sampling points at the first rate and the position information.

14. The method of claim 12, wherein determining an associated pacing signal according to a user's selection and the position information of the pacing signal, and displaying the detailed information of the associated pacing signal according to the sampling points at the first rate and the position information comprising:

detecting a heartbeat wave selected by the user on an ECG waveform in a first display area;
determining an associated pacing signal of the heartbeat wave; and
displaying in a second display area the detailed information of the associated pacing signal according to the sampling points at the first rate and the position information.

15. The method of claim 14, wherein determining the associated pacing signal associated with the heartbeat wave comprising:
calculation a distance between each pacing signal and an adjacent heartbeat wave, and
determining the associated pacing signal according to the distance between said pacing signal and said adjacent heartbeat wave.

16. The method of claim 1, further comprising:
marking a trigger position for the pacing signal on the ECG waveform according to the position information of the pacing signal.

17. The method of claim 16, wherein the trigger position marking includes one or more pacing characteristics selected from the group consisting of polarity, single-chamber pacing, biatrial pacing, or biventricular pacing.

18. An electrocardiogram (ECG) monitor, comprising:
an ECG electrode for contacting a surface of a living body and detecting an ECG signal from the living body, ECG signal including a bioelectrical signal generated by a human heart and a pacing signal generated by a pacemaker implanted in the living body;
a front-end processing device includes a first sampling unit for sampling a detected original ECG signal at a first sampling rate to form a pacing signal morphology, wherein a sampling interval of the first sampling rate is smaller than a pulse width of the pacing signal;
a first back-end processing device, which is used for recognizing the pacing signal according to sampling points at the first sampling rate and characteristics of pacing signal, performing a morphology analysis on the recognized pacing signal to obtain parameter information of the pacing signal, and which is further used for acquiring position information of the pacing signal and processing detailed information of the pacing signal into display data according to sampling points at the first sampling rate and the position information, the detailed information includes the pacing signal morphology and/or the parameter information; and
a human-machine interaction device, which is in a signal connection with the first back-end processing device and is configured to:
display, in a first area, an ECG waveform corresponding to the ECG signal, wherein the ECG waveform is obtained from the ECG signal using a second sampling rate that is less than the first sampling rate;
display, in a second area, detailed information of the pacing signal according to sampling points at the first sampling rate and the position information, the detailed information including the pacing signal morphology.

19. The ECG monitor of claim 18, wherein the first back-end processing device is further used for receiving a user selection signal detected by the human-machine interaction device and determining an associated pacing signal to be displayed according to the user's selection and the position information of the pacing signal.

20. The ECG monitor of claim 19, wherein the associated pacing signal comprises the pacing signal determined at a trigger position for the pacing signal selected by the user on an ECG waveform; or the pacing signal determined by means of a heartbeat wave selected by the user on an ECG waveform.

21. The ECG monitor of claim 20, wherein the human-machine interaction device displays the ECG waveform in a first display area, and displays the detailed information of the associated pacing signal in a second display area.

22. The ECG monitor of claim 21, wherein the first back-end processing device directly acquires the position information according to the recognized pacing signal; or the front-end processing device further includes a high-pass filter and a comparator electrically connected to each other, the high-pass filter is used for inputting with the ECG signal and outputting the pacing signal with a heartbeat filtered out, and the comparator has two signal input ends respectively for the input of the pacing signal and a threshold voltage, and has an output end connected to the first back-end processing device that determines, according to an level output by the comparator, the trigger position for the pacing signal and acquires the position information.

\* \* \* \* \*